United States Patent [19]

Heinemann et al.

[11] Patent Number: 4,642,312

[45] Date of Patent: Feb. 10, 1987

[54] N-(3-CHLORO-1,2,4-OXADIAZOL-5-YL)-UREAS

[75] Inventors: Ulrich Heinemann, Leichlingen; Hans-Joachim Knops, Monheim; Karl Steinbeck, Burscheid; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 801,452

[22] Filed: Nov. 25, 1985

[30] Foreign Application Priority Data

Dec. 12, 1984 [DE] Fed. Rep. of Germany ....... 3445205

[51] Int. Cl.$^4$ ................. A01N 47/38; C07D 271/06
[52] U.S. Cl. ................................. 514/364; 548/133
[58] Field of Search ........................ 548/133; 514/364

[56]  References Cited
U.S. PATENT DOCUMENTS 3,221,005  11/1965  Moore .............................. 548/133
3,822,280   7/1974  Moser .............................. 548/133

FOREIGN PATENT DOCUMENTS 0111442   6/1984  European Pat. Off. ........... 548/133
2801509   7/1979  Fed. Rep. of Germany ...... 548/133
 568998  11/1975  Switzerland ....................... 548/133

Primary Examiner—Robert Gerstl
Attorney, Agent, or Firm—Sprung Horn Kramer & Woods

[57]  ABSTRACT

Fungicidally active novel N-(3-chloro-1,2,4-oxadiazol-5-yl)-ureas of the formula

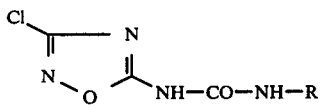

in which R is alkyl, halogenoalkyl, or optionally substituted cycloalkyl, cycloalkylalkyl or aryl.

11 Claims, No Drawings

N-(3-CHLORO-1,2,4-OXADIAZOL-5-YL)-UREAS

The invention relates to new N-(3-chloro-1,2,4-oxadiazol-5-yl)-ureas, a process for their preparation, and their use as pest-combating agents, especially as fungicides.

It is known that carbamates or imides, such as, for example, zinc ethylene-1,2-bis-(dithiocarbamate) or N-trichloromethylmercapto-phthalimide, possess fungicidal properties (see, for example, K. H. Büchel "Pflanzenschutz und Schädlingsbekämpfung" (Plant Protection and Pest-Combating), Thieme Verlag Stuttgart 1977, pages 137, 138 and 140).

However, the activity of these previously known compounds is not always completely satisfactory in all fields of use, particularly when small amounts and concentrations are used.

New N-(3-chloro-1,2,4-oxadiazol-5-yl)-ureas of the general formula (I)

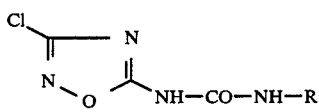

in which R represents alkyl or halogenoalkyl or represents cycloalkyl or cycloalkylalkyl, each of which is optionally substituted, or represents optionally substituted aryl,
have been found.

Furthermore, it has been found that the new N-(3-chloro-1,2,4-oxadiazol-5-yl)-ureas of the general formula (I)

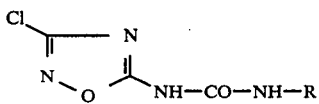

in which R represents alkyl or halogenoalkyl or represents cycloalkyl or cycloalkylalkyl, each of which is optionally substituted, or represents optionally substituted aryl,
are obtained if 5-amino-3-chloro-1,2,4-oxadiazole of the formula (II)

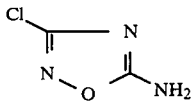

is reacted with isocyanates of the formula (III)

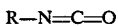 (III)

in which R has the meaning given above,
if appropriate in the presence of a diluent and, if appropriate, in the presence of a catalyst.

Finally, it has been found that the new N-(3-chloro-1,2,4-oxadiazol-5-yl)-ureas of the general formula (I) possess fungicidal properties.

Surprisingly, the N-(3-chloro-1,2,4-oxadiazol-5-yl)-ureas according to the invention, of the general formula (I), possess a substantially better activity against pests, in particular against fungi, than do the carbamates or imides such as, for example, zinc ethylene-1,2-bis-(dithiocarbamate) or N-trichloromethylthio-phthalimide, which are known from the prior art and are compounds having a similar action.

Formula (I) gives a general definition of the N-(3-chloro-1,2,4-oxadiazol-5-yl)-ureas according to the invention. Preferred compounds of the formula (I) are those
in which R represents alkyl or halogenoalkyl, each of which is straight-chain or branched and each of which has 1 to 12 carbon atoms and, where relevant, 1 to 15 identical or different halogen atoms, or represents cycloalkyl or cycloalkylalkyl, each of which has 3 to 7 carbon atoms in the cycloalkyl part and, where relevant, 1 to 6 carbon atoms in the alkyl part and each of which is optionally monosubstituted or polysubstituted in the cycloalkyl part by identical or different substituents from amongst halogen and/or straight-chain or branched alkyl having 1 to 4 carbon atoms, or represents aryl which has 6 to 10 carbon atoms and is optionally monosubstituted or polysubstituted by identical or different substituents, suitable aryl substituents being: halogen, cyano, nitro, and alkyl, alkoxy, halogenoalkyl, alkoxyalkyl, alkoxyalkyloxycarbonyl and alkoxycarbonyl, each of which is straight-chain or branched and each of which has 1 to 8 carbon atoms in the individual alkyl or alkoxy parts and, where relevant, 1 to 9 identical or different halogen atoms.

Particularly preferred compounds according to the invention, of the formula (I), are those
in which R represents alkyl or halogenoalkyl, each of which is straight-chain or branched and each of which has 1 to 6 carbon atoms and, where relevant, 1 to 9 identical or different halogen atoms, in particular fluorine, chlorine or bromine, or represents cyclopropyl, cyclopropylmethyl, cyclopropylethyl, cyclopropylpropyl, cyclobutyl, cyclopentyl, cyclohexyl or cyclohexylmethyl, each of which is optionally monosubstituted to trisubstituted in the cycloalkyl part by identical or different substituents from amongst fluorine, chlorine, bromine, methyl and ethyl, or represents phenyl or naphthyl, each of which is optionally monosubstituted to pentasubstituted by identical or different substituents, suitable substituents in each case being: fluorine, chlorine, bromine, cyano, nitro, methyl, ethyl, n- or i-propyl, n-butyl, methoxy, ethoxy, chloromethyl, dichloromethyl, trichloromethyl, trifluoromethyl, methoxymethyl, methoxyethyl, ethoxyethyl, methoxypropyl, ethoxypropyl, methoxycarbonyl, ethoxycarbonyl, propoxycarbonyl, butoxycarbonyl, pentyloxycarbonyl, methoxyethyloxycarbonyl and methoxymethoxycarbonyl.

In addition to the compounds stated in the preparation examples, the following N-(3-chloro-1,2,4-oxadiazol-5-yl)-ureas of the general formula (I) may be mentioned individually:

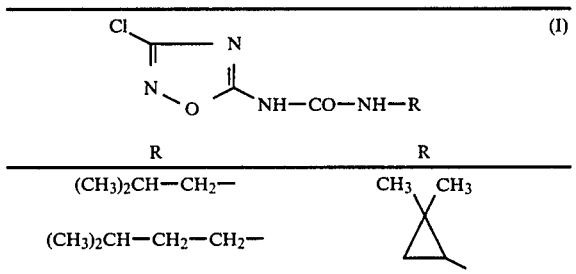

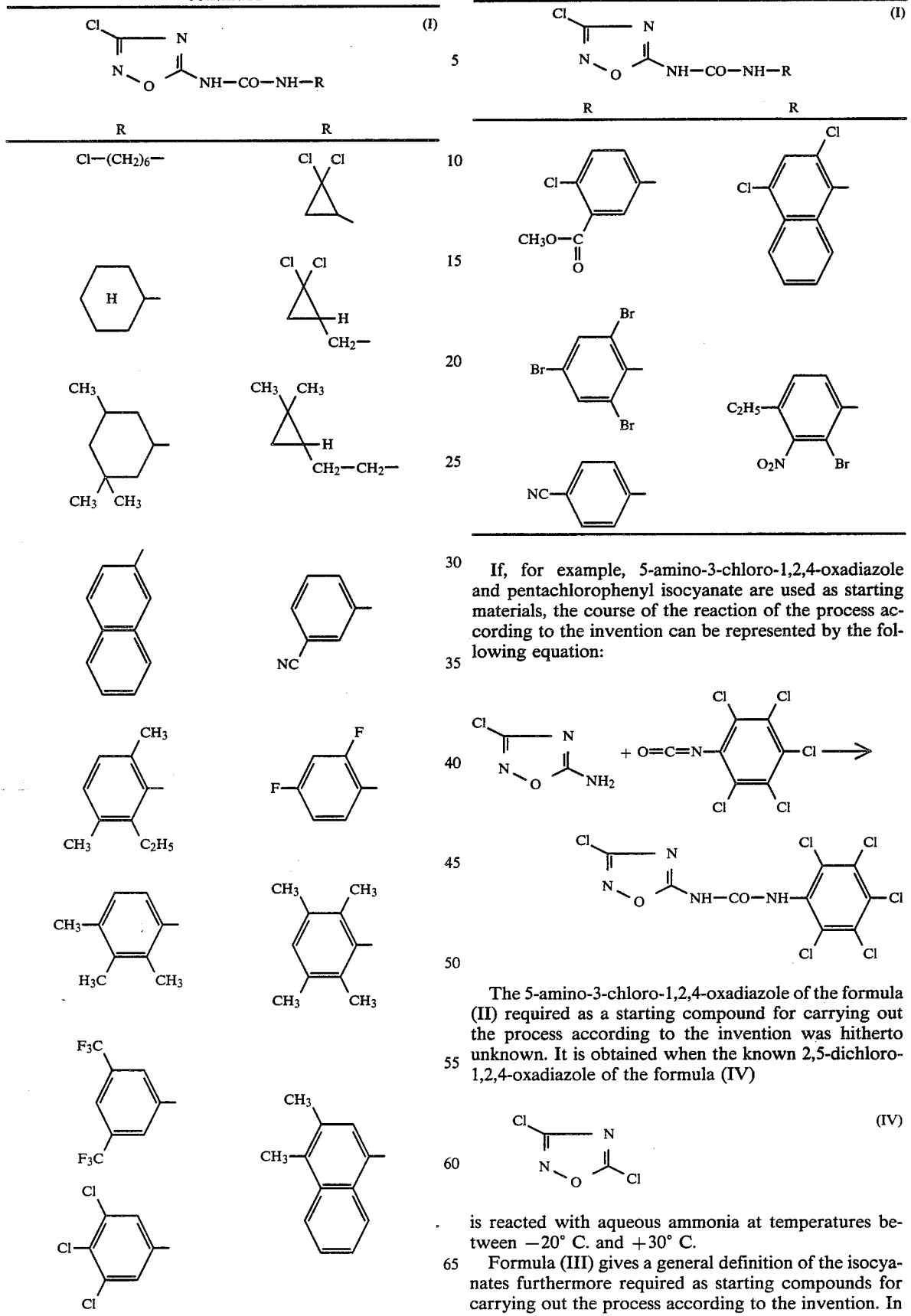

If, for example, 5-amino-3-chloro-1,2,4-oxadiazole and pentachlorophenyl isocyanate are used as starting materials, the course of the reaction of the process according to the invention can be represented by the following equation:

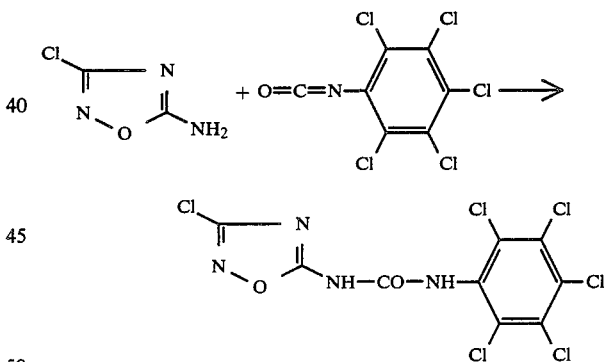

The 5-amino-3-chloro-1,2,4-oxadiazole of the formula (II) required as a starting compound for carrying out the process according to the invention was hitherto unknown. It is obtained when the known 2,5-dichloro-1,2,4-oxadiazole of the formula (IV)

is reacted with aqueous ammonia at temperatures between $-20°$ C. and $+30°$ C.

Formula (III) gives a general definition of the isocyanates furthermore required as starting compounds for carrying out the process according to the invention. In this formula (III), R preferably represents those radicals which have already been mentioned for this substituent in connection with the description of the substances according to the invention, of the formula (I).

The isocyanates of the formula (III) are generally known compounds of organic chemistry, or can be obtained in an analogous manner by methods which are known in principle.

Suitable diluents for carrying out the process according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride; ethers, such as diethyl ether, dioxane, tetrahydrofuran or ethylene glycol dimethyl or diethyl ether; ketones, such as acetone or butanone; nitriles, such as acetonitrile or propionitrile, or amides, such as dimethylformamide, dimethylacetamide, N-methylformanilide, N-methylpyrrolidone or hexamethylphosphoric acid triamide, and dimethyl sulphoxide.

The process according to the invention can, if appropriate, be carried out in the presence of a catalyst.

Suitable catalysts are all customary inorganic or organic bases. These include, for example, alkali metal carbonates, such as sodium carbonate, potassium carbonate or sodium bicarbonate; and tertiary amines, such as triethylamine, N,N-dimethylaniline, N,N-dimethylbenzylamine, pyridine, N,N-dimethylaminopyridine, diazabicyclooctane (DABCO), diazabicyclononene (DBN) and diazabicycloundecene (DBU).

In carrying out the process according to the invention, the reaction temperatures can be varied within a relatively wide range. In general, the reaction is carried out at temperatures between 20° C. and 160° C., preferably between 60° C. and 140° C.

To carry out the process according to the invention, 1 to 3 moles, preferably 1 to 2 moles, of the isocyanate of the formula (III) and, if appropriate, 0.001 to 1.5 moles of the catalyst are generally employed per mole of 5-amino-3-chloro-1,2,4-oxadiazole of the formula (II). The reaction procedure, working-up and isolation of the reaction products of the formula (I) are carried out by generally customary methods.

The active compounds according to the invention exhibit a powerful microbicidal action and can be employed in practice for combating undesired microorganisms. The active compounds are suitable for use as plant protection agents, especially as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases included under the abovementioned main headings, are mentioned below as non-limiting examples:

Botrytis species, such as, for example, Botrytis cinerea; Plasmopara species, such as, for example, Plasmopara viticola; Uromyces species, such as, for example, *Uromyces appendiculatus;* Sphaerotheca species, such as, for example, *Sphaerotheca fuliginea;* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustiliago species, such as, for example, *Utilago nuda* or *Ustilago avenae;* Septoria species, such as, for example, *Septoria nodorum;* Tilletia species, such as, for example, *Tilletia caries;* Pyricularia species, such as, for example, *Pyricularia oryzae;* Pellicularia species, such as, for example, *Pellicularia sasakii;* Erwinia species, such as, for example, *Erwinia amylovora;* Pyrenophora species, such as, for example, *Pyrenophora teres;* (conidea form; Dreshslera, Syn: Helminthosporium); Leptosphaeria species, such as, for example, *Leptosphaeria nodorum;* Cochliobolus species, such as, for example, *Cochliobolus sativus* (conidea form: Dreschslera, Syn: Helminthosphorium) and Cercospora species, such as, for example, *Cercospora canescens.*

The good toleration by plants, of the active compounds, at the concentrations required for combating plant diseases, permits treatment of above-ground parts of plants, of vegetative propagation stock and seeds, and of the soil.

The active compounds according to the invention can be used with particularly good success for combating cereal diseases, for example those caused by *Leptosphaeria nodorum, Cochliobolus sativus,* Fusarium species or *Pyrenophora teres,* for combating rice diseases, such as, for example, against the blast disease of rice causative organism [*Pyricularia oryzae*], and for combating grapevine diseases, such as, for example, against the downy mildew of grapevine causative organism (*Plasmorpara viticola*). In this respect, the active compounds according to the invention exhibit not only outstanding protective properties but also very good systemic activity.

When used in appropriately larger amounts, the active compounds according to the invention also have a herbicidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of the surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellents, such as halogenated hydrocarbons as well as butane, propane, nitrogen, and carbon dioxide; as solid carriers: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, foaming, brushing on, dusting, scattering, dry dressing, moist dressing, wet dressing, slurry dressing or encrusting.

When used as leaf fungicides, the active compound concentrations in the use forms can be varied within a substantial range. They are, in general, between 1 and 0.0001 percent by weight, preferably between 0.5 and 0.001%.

In the treatment of seed, amounts of active compound of 0.001 to 50 g per kilogram of seed, preferably 0.01 to 10 g, are generally required.

For the treatment of soil, amounts of active compound of 0.00001 to 0.1% by weight, preferably 0.0001 to 0.02% by weight, are required at the place of action.

PREPARATION EXAMPLES

Example 1

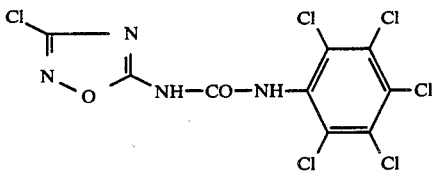

11.9 g (0.1 mole) of 5-amino-3-chloro-1,2,4-oxadiazole and 29.1 g (0.1 mole) of pentachlorophenyl isocyanate are heated under reflux for 4 hours together with a few drops of dimethylbenzylamine in 100 ml of dry toluene. After the mixture has been cooled to room temperature, the precipitated solid is filtered off under suction and rinsed several times with ether.

32 g (78% of theory) of N-(3-chloro-1,2,4-oxadiazol-5-yl)-N'-pentachlorophenyl-urea of melting point 258° C. are obtained.

The following N-(3-chloro-1,2,4-oxadiazol-5-yl)ureas of the general formula (I):

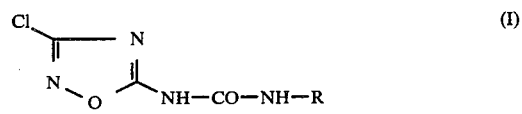

are obtained in a corresponding manner and in accordance with the general preparation data:

| Example No. | R | Melting point [°C.] |
|---|---|---|
| 2 | 3,4-dichlorophenyl | 235 |
| 3 | phenyl | 164 |
| 4 | 3-(trifluoromethyl)phenyl | 170–175 |
| 5 | 4-chlorophenyl | 194–197 |
| 6 | 3-chlorophenyl | 199–202 |
| 7 | 3,4-dichlorophenyl (Cl-/Cl-) | 195–197 |
| 8 | 2,4-dichlorophenyl | 186–190 |
| 9 | 4-ethoxyphenyl (C₂H₅O-) | 162–163 |

-continued

| Example No. | R | Melting point [°C.] |
|---|---|---|
| 10 | 2,3-dichlorophenyl | 192 (decomposition) |
| 11 | 2,4,5-trichlorophenyl | 219–230 |
| 12 | 2-chloro-3-methylphenyl | 178–179 |
| 13 | 2,3-dimethylphenyl | 172–175 (decomposition) |
| 14 | 3-chloro-4-methylphenyl | 132–135 |
| 15 | 2-chloro-5-nitrophenyl | >186 (decomposition) |
| 16 | 2,5-dichlorophenyl | >250 (decomposition) |
| 17 | 2-methyl-3-nitrophenyl | 160 |
| 18 | Cl,CCl₃-phenyl | 155–159 (decomposition) (pure substance, assignment of the chlorine atom not possible) |
| 19 | 2,4-dimethylphenyl | 159 |
| 20 | 2,6-dimethylphenyl | 140–145 |
| 21 | 4-(CCl₃)-phenyl | >250 |
| 22 | 3-methylphenyl | >176 (decomposition) |
| 23 | CH₃—(CH₂)₂— | 147–148 |
| 24 | CH₃ | 208 |
| 25 | C₂H₅ | 173–176 |
| 26 | CH₃—(CH₂)₃— | 140 |
| 27 | 2-chloro-4-(CHF₂)-phenyl | 217–221 |
| 28 | 2-chloro-6-methylphenyl | >247 (decomposition) |
| 29 | 2-methyl-3-methoxyphenyl | 145–153 |
| 30 | 1-naphthyl | >248 (decomposition) |
| 31 | 3,4-dimethoxyphenyl | >218 (decomposition) |
| 32 | 2-(ClCH₂)-4-chlorophenyl | >186 (decomposition) |
| 33 | 3-chloro-4-methylphenyl | >186 (decomposition) |
| 34 | CH₃(CH₂)₄—O—C(=O)— (2-chlorophenyl ester) | oil |
| 35 | 2-chloro-5-(C(=O)O—CH₂—CH₂—OCH₃)-phenyl | 107–111 |
| 36 | 2,4-dichloro-5-methylphenyl | 237 |
| 37 | 2-chloro-4-(ClCH₂)-phenyl | >138 (decomposition) |
| 38 | 2-isopropylphenyl | >162 (decomposition) |

-continued

| Example No. | R | Melting point [°C] |
|---|---|---|
| 39 | n-C$_4$H$_9$—⟨phenyl⟩— | 155–58 |
| 40 | CH$_3$—⟨phenyl⟩— | >194 (decomposition) |
| 41 | CF$_3$—⟨phenyl with Cl⟩— | 171–75 |

PREPARATION OF THE STARTING COMPOUND

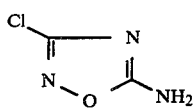

A mixture of 108 g (0.8 mole) of 25 percent strength aqueous ammonia solution and 100 ml of water is added dropwise to 100 g (0.72 mole) of 3,5-dichloro-1,2,4-oxadiazole at 20° C. (cooling), while stirring. The addition lasts for about 1.5 hours. When the addition is complete, stirring is continued for a further 3 hours at room temperature, and the precipitate which has separated out is filtered off under suction and recrystallized from water.

67.8 g (79% of theory) of 5-amino-3-chloro-1,2,4-oxadiazole of melting point 169° C.–171° C. are obtained.

USE EXAMPLES

In the following use examples, the compounds listed below were employed as comparative substances:

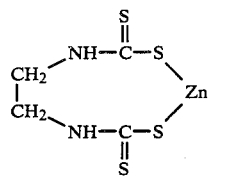

(A)

Zinc ethylene-1,2-bis-(dithiocarbamate) and

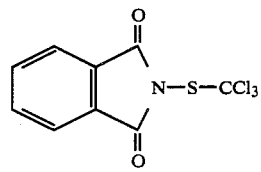

(B)

N-Trichloromethylthio-phthalimide

Example A

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 1, 10, 17 and 25.

Example B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 1, 2, 5, 7, 8 and 11.

Example C

Leptosphaeria nodorum test (wheat)/protective
Solvent: 100 parts by weight of dimethyl formamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 2, 5 and 7.

Example D

Plasmopara test (vines)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, a clearly superior activity compared with the prior art is shown, for example, by the compounds according to preparation examples: 2, 7 and 8.

It will be understood that the specification and examples are illustrative but not limitative of the present invention and that other embodiments within the spirit and scope of the invention will suggest themselves to those skilled in the art.

What is claimed is:

1. An N-(3-chloro-1,2,4-oxadiazol-5-yl)-urea of the formula

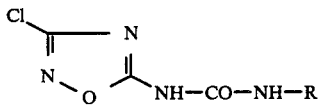

in which R is alkyl or halogenoalkyl each of which has 1 to 12 carbon atoms and, where relevant, 1 to 15 halogen atoms, or is cycloalkyl or cycloalkylalkyl each of which has 3 to 7 carbon atoms in the cycloalkyl part and, where relevant, 1 to 6 carbon atoms in the alkyl part and each of which is optionally substituted in the cycloalkyl part by halogen and/or alkyl having 1 to 4 carbon atoms, or is aryl which has 6 to 10 carbon atoms and is optionally substituted by halogen, cyano, nitro, alkyl, alkoxy, halogenoalkyl with up to 9 halogen atoms, alkoxyalkyl, alkoxyalkyloxycarbonyl and/or alkoxycarbonyl, the various alkyl and alkoxy moieties having up to 8 carbon atoms.

2. An N-(3-chloro-1,2,4-oxadiazol-5-yl)-urea according to claim 1,
in which R is alkyl or halogenoalkyl each of which has 1 to 6 carbon atoms and, where relevant, 1 to 9 halogen atoms, or is cyclopropyl, cyclopropylmethyl, cyclopropylethyl, cyclopropylpropyl, cyclobutyl, cyclopentyl, cyclohexyl or cyclohexylmethyl, each of which is optionally monosubstituted to trisubstituted in the cycloalkyl part by fluorine, chlorine, bromine, methyl and/or ethyl, or is phenyl or naphthyl each of which is optionally monosubstituted to pentasubstituted by fluorine, chlorine, bromine, cyano, nitro, methyl, ethyl, n- or i-propyl, n-butyl, methoxy, ethoxy, chloromethyl, dichloromethyl, trichloromethyl, trifluoromethyl, methoxymethyl, methoxyethyl, ethoxyethyl, methoxypropyl, ethoxypropyl, methoxycarbonyl, ethoxycarbonyl, propoxycarbonyl, butoxycarbonyl, pentyloxycarbonyl, methoxyethyloxycarbonyl and/or methoxymethoxycarbonyl.

3. A compound according to claim 1, wherein such compound is N-(3-chloro-1,2,4-oxadiazol-5-yl)-N'-pentachlorophenyl-urea of the formula

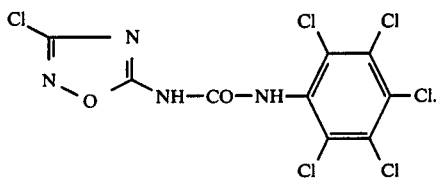

4. A compound according to claim 1, wherein such compound is N-(3-chloro-1,2,4-oxadiazol-5-yl)-N'-3,5-dichlorophenyl-urea of the formula

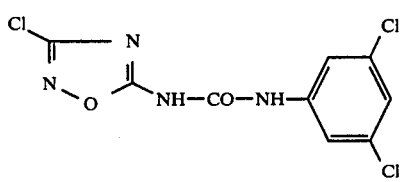

5. A compound according to claim 1, wherein such compound is N-(3-chloro-1,2,4-oxadiazol-5-yl)-N'-4-chlorophenyl-urea of the formula

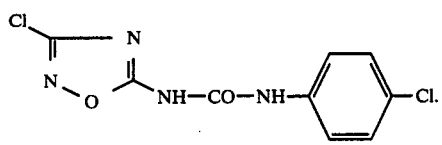

6. A compound according to claim 1, wherein such compound is N-(3-chloro-1,2,4-oxadiazol-5-yl)-N'-3,4-dichlorophenyl-urea of the formula

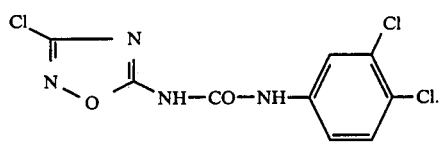

7. A compound according to claim 1, wherein such compound is N-(3-chloro-1,2,4-oxadiazol-5-yl)-N'-2,4-dichlorophenyl-urea of the formula

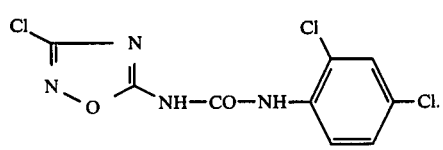

8. A fungicidal composition comprising a fungicidally effective amount of a compound according to claim 1 and a diluent.

9. A method of combating fungi which comprises applying to such fungi or to a fungus habitat a fungicidally effective amount of a compound according to claim 1.

10. The method according to claim 9, wherein such compound is

N-(3-chloro-1,2,4-oxadiazol-5-yl)-N'-pentachlorophenyl-urea,
N-(3-chloro-1,2,4-oxadiazol-5-yl)-N'-3,5-dichlorophenyl-urea,
N-(3-chloro-1,2,4-oxadiazol-5-yl)-N'-4-chlorophenyl-urea,
N-(3-chloro-1,2,4-oxadiazol-5-yl)-N'-3,4-dichlorophenyl-urea or
N-(3-chloro-1,2,4-oxadiazol-5-yl)-N'-2,4-dichlorophenylurea.
11. 5-Amino-3-chloro-1,2,4-oxadiazole of the formula
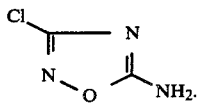
* * * * *